US010123958B2

(12) United States Patent
Banowski et al.

(10) Patent No.: US 10,123,958 B2
(45) Date of Patent: *Nov. 13, 2018

(54) ANTIPERSPIRANT COSMETICS COMPRISING SPECIFIC PROTEINS FROM LEGUMES OF THE GENUS *PISUM* AND/OR *PHASEOLUS* AND/OR *VIGNA* AND/OR *MACROTYLOMA* OR FROM CRUCIFEROUS PLANTS OF THE GENUS *BRASSICA* AND INCLUDING NO ALUMINUM AND/OR ZIRCONIUM HALIDES AND/OR HYDROXY HALIDES

(71) Applicant: Henkel AG & Co. KGaA, Duesseldorf (DE)

(72) Inventors: Bernhard Banowski, Duesseldorf (DE); Stefan Evers, Haan (DE)

(73) Assignee: Henkel AG & Co. KGaA (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/400,773

(22) Filed: Jan. 6, 2017

(65) Prior Publication Data

US 2017/0112747 A1 Apr. 27, 2017

Related U.S. Application Data

(63) Continuation of application No. PCT/EP2015/064993, filed on Jul. 1, 2015.

(30) Foreign Application Priority Data

Jul. 8, 2014 (DE) .................. 10 2014 213 227
Aug. 26, 2014 (DE) .................. 10 2014 216 908

(51) Int. Cl.
*A61K 8/64* (2006.01)
*A61K 8/92* (2006.01)
*A61Q 15/00* (2006.01)
*A61K 8/97* (2017.01)

(52) U.S. Cl.
CPC .............. *A61K 8/64* (2013.01); *A61K 8/645* (2013.01); *A61K 8/92* (2013.01); *A61K 8/97* (2013.01); *A61Q 15/00* (2013.01); *A61K 2800/30* (2013.01)

(58) Field of Classification Search
CPC . A61K 8/645; A61K 8/97; A61K 8/64; A61K 8/92; A61K 2800/30; A61Q 15/00
See application file for complete search history.

(56) References Cited

U.S. PATENT DOCUMENTS 5,322,839 A 6/1994 Voegeli et al.
8,697,151 B2 4/2014 Contet-Audonneau et al.
9,199,101 B2 12/2015 Dal Farra et al.
2005/0019301 A1 1/2005 Contet-Audonneau et al.
2010/0028272 A1* 2/2010 Knappe ............... A61K 8/8152 424/47
2013/0029917 A1* 1/2013 Dal Farra ............... A61K 8/97 514/18.8
2013/0280175 A1 10/2013 Banowski et al.
2014/0228268 A1* 8/2014 Fahl .................... A61Q 5/02 510/127

FOREIGN PATENT DOCUMENTS

| DE | 102010055816 A1 | 6/2012 |
| DE | 102012222692 A1 | 9/2013 |
| EP | 1813310 A2 | 8/2007 |
| EP | 2143418 A1 | 1/2010 |
| FR | 2796839 A1 | 2/2001 |
| FR | 2944446 A1 | 10/2010 |
| FR | 2971159 A1 | 8/2012 |
| WO | 94/24993 A1 | 11/1994 |
| WO | 2010/003861 A1 | 1/2010 |
| WO | 2010/070143 A1 | 6/2010 |
| WO | WO 2014/165490 A2 * | 10/2014 |

OTHER PUBLICATIONS

PCT International Search Report (PCT/EP2015/064993) dated Oct. 9, 2015.
Moore et al., "Chromatography of Amino Acids on Sulfonated Polystyrene Resins", Journal of Biological Chemistry, vol. 192, pp. 663-681, 1951.
Andrews, "Estimation of the Molecular Weights of Proteins by Sephadex Gel-Filtration" Biochemical Journal, vol. 91, pp. 222-233, 1964.
Geria, "Formulation of Stick Antiperspirants and Deodorants", Cosmetics & Toiletries, vol. 99, pp. 55-66, 1984.
Oliveira et al., "Evaluation of Metal Ions in Rice Samples: Extraction and Direct Determination by ICP OES", Journal of the Brazilian Chemical Society, vol. 23, No. 5, pp. 838-845, 2012.
Database GNPD Mintel, "24H Anti-Perspirant Deodorant Spray", XP002744351, Database Accession No. 2301648, 2014.

* cited by examiner

*Primary Examiner* — Doan Thi-Thuc Phan
(74) *Attorney, Agent, or Firm* — P. Scott Smith

(57) ABSTRACT

The present invention relates to an antiperspirant cosmetic agent including at least one specific protein from legumes of the genus *Pisum* and/or *Phaseolus* and/or *Vigna* and/or *Macrotyloma* or from cruciferous plants of the genus *Brassica* and including no aluminum and/or zirconium halides and/or hydroxyhalides. The present invention further relates to the use of a specific protein and to a non-therapeutic method for reducing body perspiration. Adding or using said at least one specific protein ensures that the sweat gland(s) are effectively influenced, thus resulting in a significant reduction in axillary sweat even in the absence of antiperspirant aluminum salts.

18 Claims, No Drawings

ANTIPERSPIRANT COSMETICS COMPRISING SPECIFIC PROTEINS FROM LEGUMES OF THE GENUS *PISUM* AND/OR *PHASEOLUS* AND/OR *VIGNA* AND/OR *MACROTYLOMA* OR FROM CRUCIFEROUS PLANTS OF THE GENUS *BRASSICA* AND INCLUDING NO ALUMINUM AND/OR ZIRCONIUM HALIDES AND/OR HYDROXY HALIDES

FIELD OF THE INVENTION

The present invention generally relates to an antiperspirant cosmetic agent without aluminum and/or zirconium halides and/or hydroxyhalides, which includes at least one substance selected from the group of cosmetic oils that are liquid at 20° C. and 1,013 hPa, odorous substances, and waxes, optionally at least one propellant, and specific proteins from legumes of the genus *Pisum* and/or *Phaseolus* and/or *Vigna* and/or *Macrotyloma* or from cruciferous plants of the genus *Brassica*. The addition of the at least one specific protein results in an effect on the sweat gland(s).

Furthermore, the present invention relates to a packaging unit (kit of parts), containing a cosmetic agent according to the invention and a cosmetic agent having at least one antiperspirant active substance.

The present invention also relates to the use of specific proteins from legumes of the genus *Pisum* and/or *Phaseolus* and/or *Vigna* and/or *Macrotyloma* or from cruciferous plants of the genus *Brassica* to at least partially affect the sweat gland(s).

In addition, the present invention relates to the use of a combination, including at least one substance selected from the group of cosmetic oils that are liquid at 20° C. and 1,013 hPa, odorous substances, and waxes, optionally at least one propellant, and specific proteins from legumes of the genus *Pisum* and/or *Phaseolus* and/or *Vigna* and/or *Macrotyloma* or from cruciferous plants of the genus *Brassica*, to reduce and/or prevent sweat, particularly axillary sweat or sweat of other body regions. The combination according to the invention includes no aluminum and/or zirconium halides and/or hydroxyhalides.

Furthermore, the present invention relates to an antiperspirant cosmetic agent without aluminum and/or zirconium halides and/or hydroxyhalides, which includes at least one substance selected from the group of cosmetic oils that are liquid at 20° C. and 1,013 hPa, odorous substances, and waxes, optionally at least one propellant, and at least one specific protein that is isolated from legumes of the genus *Pisum* or at least one protein that is isolated from the group of rape, cauliflower, red cabbage, savoy cabbage, white cabbage, pointed cabbage, Brussels sprouts, kohlrabi, curly kale, broccoli, mustard, turnips and mixtures thereof and optionally hydrolyzed. The addition of the at least one specific protein results in an effect on the sweat gland(s).

Finally, the present invention relates to a non-therapeutic cosmetic method for preventing and/or reducing the perspiration of the body, wherein an antiperspirant cosmetic agent according to the invention is applied to the skin, particularly to the skin of the axillae, and remains on the skin of the axillae for at least 1 hour, preferably for at least 2 hours, more preferably for at least 4 hours, particularly for at least 6 hours.

BACKGROUND OF THE INVENTION

The washing, cleaning, and care of one's own body is a basic human need, and modern industry is continually attempting to meet these human needs in a variety of ways. Especially important for daily hygiene is the lasting elimination or at least reduction of body odor and axillary moisture. Numerous specific deodorizing or antiperspirant body care agents developed for use in body regions having a high density of sweat glands, particularly in the axillary region, are known in the prior art. Said body care agents are formulated in a wide range of product forms, for example as a powder, stick, aerosol spray, pump spray, liquid and gel roll-on application, cream, gel, and impregnated flexible substrates (deodorant wipes).

Cosmetic antiperspirants of the prior art include, in addition to at least one oil or wax and one odorous substance component or perfume, at least one antiperspirant compound, particularly in the form of aluminum and/or zirconium halides and/or hydroxyhalides. Said antiperspirant compounds reduce the secretion of sweat of the body by temporarily constricting and/or plugging the excretory ducts of the sweat glands so that the amount of sweat can be reduced by approximately 20 to 60 percent. Furthermore, said antiperspirant compounds have an additional deodorizing effect because of the antimicrobial action of said antiperspirant compounds.

Aluminum and/or zirconium halides and/or hydroxyhalides, in conjunction with the acidic pH value of these antiperspirants, can lead to unpleasant skin reactions for some users. Furthermore, the use of the aforementioned antiperspirant compounds can lead to stains on clothing.

Therefore, there is a need for replacing antiperspirant aluminum and/or zirconium halides and/or hydroxyhalides with other antiperspirant cosmetic active substances. Said antiperspirant active substances should have good antiperspirant action and good skin compatibility and should be easy to formulate. Furthermore, said antiperspirant active substances should not have a negative effect on the storage stability of the antiperspirant cosmetic agents.

The present invention addresses the problem of providing an antiperspirant cosmetic agent that avoids or at least lessens the disadvantages of the prior art and that has good skin compatibility and also reliably reduces axillary moisture. Furthermore, the antiperspirant cosmetic agent should have high storage stability.

It has now surprisingly been found that, if at least one protein from legumes of the genus *Pisum* and/or *Phaseolus* and/or *Vigna* and/or *Macrotyloma* or from cruciferous plants of the genus *Brassica* that causes a change in the light absorption of 1 to 100% in the event of a change in the pH value of at least 0.5 in a pH range of pH 4.0 to pH 8.0 is used in cosmetic agents without antiperspirant aluminum and/or zirconium halides and/or hydroxyhalides, the result is antiperspirant action that is nearly comparable to the antiperspirant action of formulations having aluminum salts and/or aluminum-zirconium complexes.

Furthermore, other desirable features and characteristics of the present invention will become apparent from the subsequent detailed description of the invention and the appended claims, taken in conjunction with this background of the invention.

BRIEF SUMMARY OF THE INVENTION

An antiperspirant cosmetic agent, including at least one substance selected from the group of cosmetic oils that are liquid at 20° C. and 1,013 hPa, odorous substances, and waxes; propellant in a total amount of 0 to 99 wt %, with respect to the total weight of the antiperspirant cosmetic agent; and at least one protein in a total amount of 0.1 to 70 wt %, with respect to the total weight of the antiperspirant cosmetic agent, wherein the at least one protein occurs in legumes of the genus *Pisum* and/or *Phaseolus* and/or *Vigna* and/or *Macrotyloma* or in cruciferous plants of the genus *Brassica* and wherein the at least one protein causes a change in the light absorption of 1 to 100% in the event of a pH value change of at least 0.5 in a pH range of pH 4.0 to pH 8.0, at a temperature of 20° C. to 40° C. and a concentration of the protein of 0.001 to 10 wt %, with respect to the total weight of the sample mixture used to determine the change in the light absorption, wherein the antiperspirant cosmetic agent includes no aluminum and/or zirconium halides and/or hydroxyhalides.

A packaging unit (kit of parts), comprising—formulated separate from each other—at least one first container (C1), including a cosmetic agent (M1) comprising at least one antiperspirant active substance; and at least one second container (C2), including a cosmetic agent (M2) comprising at least one protein, wherein the at least one protein occurs in legumes of the genus *Pisum* and/or *Phaseolus* and/or *Vigna* and/or *Macrotyloma* or in cruciferous plants of the genus *Brassica*, wherein the at least one protein causes a change in the light absorption of 1 to 100% in the event of a pH value change of at least 0.5 in a pH range of pH 4.0 to pH 8.0, at a temperature of 20° C. to 40° C. and a concentration of the protein of 0.001 to 10 wt %, with respect to the total weight of the sample mixture used to determine the change in the light absorption, and wherein the cosmetic agent (M2) includes no aluminum and/or zirconium halides and/or hydroxyhalides.

The use of at least one protein to at least partially influence the sweat gland(s), wherein the at least one protein occurs in legumes of the genus *Pisum* and/or *Phaseolus* and/or *Vigna* and/or *Macrotyloma* or in cruciferous plants of the genus *Brassica* and wherein the at least one protein causes a change in the light absorption of 1 to 100% in the event of a pH value change of at least 0.5 in a pH range of pH 4.0 to pH 8.0, at a temperature of 20° C. to 40° C. and a concentration of the protein of 0.001 to 10 wt %, with respect to the total weight of the sample mixture used to determine the change in the light absorption.

The use of a combination, including at least one substance selected from the group of cosmetic oils that are liquid at 20° C. and 1,013 hPa, odorous substances, and waxes; propellant in a total amount of 0 to 99 wt %, with respect to the total weight of the antiperspirant cosmetic agent; and at least one protein in a total amount of 0.1 to 70 wt %, with respect to the total weight of the antiperspirant cosmetic agent, wherein the at least one protein occurs in legumes of the genus *Pisum* and/or *Phaseolus* and/or *Vigna* and/or *Macrotyloma* or in cruciferous plants of the genus *Brassica*, wherein the at least one protein causes a change in the light absorption of 1 to 100% in the event of a pH value change of at least 0.5 in a pH range of pH 4.0 to pH 8.0, at a temperature of 20° C. to 40° C. and a concentration of the protein of 0.001 to 10 wt %, with respect to the total weight of the sample mixture used to determine the change in the light absorption, and wherein the combination includes no aluminum and/or zirconium halides and/or hydroxyhalides, to reduce and/or prevent sweat, particularly axillary sweat or sweat of other body regions.

An antiperspirant cosmetic agent, including at least one substance selected from the group of cosmetic oils that are liquid at 20° C. and 1,013 hPa, odorous substances, and waxes; propellant in a total amount of 0 to 99 wt %, with respect to the total weight of the antiperspirant cosmetic agent; and at least one protein isolated from legumes of the genus *Pisum* in a total amount of 0.1 to 70 wt %, with respect to the total weight of the antiperspirant cosmetic agent, wherein the protein is hydrolyzed and optionally cationically modified, or at least one protein that occurs in rape and/or cauliflower and/or red cabbage and/or savoy cabbage and/or white cabbage and/or pointed cabbage and/or Brussels sprouts and/or kohlrabi and/or curly kale and/or broccoli and/or mustard and/or turnips, which protein preferably occurs in rape seed and is optionally hydrolyzed, in a total amount of 0.1 to 70 wt %, with respect to the total weight of the antiperspirant cosmetic agent, wherein the antiperspirant cosmetic agent includes no aluminum and/or zirconium halides and/or hydroxyhalides.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

The subject of the present invention is an antiperspirant cosmetic agent, including a) at least one substance selected from the group of cosmetic oils that are liquid at 20° C. and 1,013 hPa, odorous substances, and waxes, b) propellant in a total amount of 0 to 99 wt %, with respect to the total weight of the antiperspirant cosmetic agent, and c) at least one protein in a total amount of 0.1 to 70 wt %, with respect to the total weight of the antiperspirant cosmetic agent, wherein the at least one protein occurs in legumes of the genus *Pisum* and/or *Phaseolus* and/or *Vigna* and/or *Macrotyloma* or in cruciferous plants of the genus *Brassica* and wherein the at least one protein causes a change in the light absorption of 1 to 100% in the event of a pH value change of at least 0.5 in a pH range of pH 4.0 to pH 8.0, at a temperature of 20° C. to 40° C. and a concentration of the protein of 0.001 to 10 wt %, with respect to the total weight of the sample mixture used to determine the change in the light absorption, wherein the antiperspirant cosmetic agent includes no aluminum and/or zirconium halides and/or hydroxyhalides.

The use of the at least one protein from legumes of the genus *Pisum* and/or *Phaseolus* and/or *Vigna* and/or *Macrotyloma* or from cruciferous plants of the genus *Brassica* having the specific physical properties mentioned above in the antiperspirant cosmetic agents according to the invention results in a deliberate effect on the sweat gland(s), though there is no intention of being restricted to this theory. Said deliberate effect on the sweat gland(s) can consist, for example, in gel formation by the at least one protein at pH values that exist only within the excretory ducts of the sweat glands. In this way, effective plugging of the excretory ducts of the sweat glands can be ensured without a reduction in the antiperspirant action of the cosmetic agent according to the invention because of premature undesired gel formation due to the addition of the at least one specific protein. However, the deliberate effect on the sweat gland(s) can also consist in a disturbance of the charge equilibrium within the sweat gland(s), which leads to an effect on the production of sweat, particularly to a reduction in the production of sweat. Therefore, an effective reduction in axillary sweat is ensured even in the absence of antiperspirant aluminum and/or zirconium halides and/or hydroxyhalides.

According to the invention, the term "antiperspirant" is understood to mean the reduction of the perspiration of the sweat glands of the body.

Furthermore, in the context of the present invention, the term "aluminum and/or zirconium halides and/or hydroxyhalides" is understood to mean, in particular, chlorides, bromides, and iodides of aluminum and zirconium and compounds of the formulas $Al(OH)_yX$ and $Zr(OH)_zX$, wherein X represents a halide ion in the aforementioned formulas.

Furthermore, in the sense of the present invention, the term "cosmetic oil" is understood to mean an oil that is suitable for cosmetic use and that is not miscible with water in all amounts. The cosmetic oil used according to the invention is neither an odorous substance nor an essential oil.

In addition, in the sense of the present invention, the term "odorous substances" is understood to mean substances that have a molar mass of 74 to 300 g/mol, that include at least one osmophore in the molecule, and that have an odor and/or flavor, i.e., said substances are capable of stimulating the receptors of the hair cells of the olfactory system. Osmophores are groups, in the form of hydroxy groups, formyl groups, oxo groups, alkoxycarbonyl groups, nitrile groups, nitro groups, azide groups, etc., that are covalently bonded to the molecular skeleton. In this context, perfume oils, perfumes, or perfume oil constituents that are liquid at 20° C. and 1,013 hPa also fall under the term "odorous substances" in the sense of the present invention.

Furthermore, in the context of the present invention, the term "waxes" is understood to mean substances that are kneadable or solid to brittle and hard at 20° C., have a coarse to finely crystalline structure, and are colorfully translucent to opaque, but not vitreous. Furthermore, said substances melt above 25° C. without decomposition, flow readily (have low viscosity) slightly above the melting point, have a highly temperature-dependent consistency and solubility, and can be polished under light pressure.

According to the invention, the term "protein" refers to chemical compounds that are condensation products of amino acids, which condensation products are linked by peptide bonds in the manner of an acid amide. The number of amino acids in the proteins is preferably at least 2 and at most 1,000 amino acids. According to the invention, the term "protein" should also be understood to mean hydrolysates of a protein that include protein fractions having different amino acid sequences and molecular weights. Furthermore, in the context of the present invention, this term should also be understood to mean mixtures of proteins that occur in legumes of the genus *Pisum* and/or *Phaseolus* and/or *Vigna* and/or *Macrotyloma* or in cruciferous plants of the genus *Brassica*.

Furthermore, in the context of the present invention, the term "legumes" should be understood to mean plants that form a pod (also called legume) from only one carpel, which pod splits open at a front seam and a back seam at maturity. However, according to the invention, this term is also understood to mean the seeds, particularly the ripe seeds, of the aforementioned plants.

In addition, in the context of the present invention, the term "cruciferous plants" should be understood to means plants of the order Brassicales that have four-petal perfect flowers. The most well-known cultivated plants in the family of the cruciferous plants include, for example, rape, cabbage types, such as cauliflower, red cabbage, savoy cabbage, white cabbage, pointed cabbage, Brussels sprouts, kohlrabi, curly kale, or broccoli, mustard, and turnips, such as Swedish turnips. Proteins that can be isolated from the cultivated plant rape are especially preferably used in the context of the present invention.

Furthermore, the term "change in the light absorption of the at least one protein" is understood to mean the positive and negative change in the light transmittance of the sample mixture, particularly of the protein solution, and is also understood to mean the absorption of light by the at least one protein or the sample mixture.

Furthermore, the term "pH value change" is understood to mean continuous change in the pH value. Continuous change in the pH value can be achieved, for example, by the titration, or steady addition, of a base or acid.

According to the invention, the term "sample mixture" refers to a mixture of the at least one specific protein with a solvent, particularly water, buffer, or salt-including aqueous solutions.

In addition, the term "fatty acids," as it is used in the context of the present invention, should be understood to mean aliphatic carboxylic acids that have unbranched or branched carbon residues having 4 to 40 carbon atoms. The fatty acids used in the context of the present invention can be naturally occurring fatty acids or synthetically produced fatty acids. Furthermore, the fatty acids can be mono- or polyunsaturated.

Finally, in the context of the present invention, the term "fatty alcohols" should be understood to mean aliphatic, monohydric, primary alcohols that have unbranched or branched hydrocarbon residues having 4 to 40 carbon atoms. The fatty alcohols used in the context of the invention can also be mono- or polyunsaturated.

In this document, the specification of wt % relates to the total weight of the antiperspirant cosmetic agents according to the invention, unless otherwise indicated.

As a first constituent a), the cosmetic agents according to the invention include at least one substance selected from the group of cosmetic oils that are liquid at 20° C. and 1,013 hPa, odorous substances, and waxes.

In the context of the present invention, the cosmetic oil that is liquid at 20° C. and 1,013 hPa is selected from the group of (i) volatile cyclic silicone oils, particularly cyclic and linear silicone oils; (ii) volatile non-silicone oils, particularly liquid paraffin oils and isoparaffin oils; (iii) non-volatile silicone oils; (iv) non-volatile non-silicone oils; and (v) mixtures thereof.

According to the invention, the term "volatile oil" refers to oils that have a vapor pressure of 2.66 Pa to 40,000 Pa (0.02 to 300 mm Hg), preferably 10 to 12,000 Pa (0.1 to 90 mm Hg), more preferably 13 to 3,000 Pa (0.1 to 23 mm Hg), particularly 15 to 500 Pa (0.1 to 4 mm Hg), at 20° C. and an ambient pressure 1,013 hPa.

Furthermore, in the sense of the present invention, the term "non-volatile oils" is understood to mean oils that have a vapor pressure of less than 2.66 Pa (0.02 mm Hg) at 20° C. and an ambient pressure of 1,013 hPa.

According to the invention, it can be preferred that mixtures of volatile silicone oils and volatile non-silicone oils are used in the antiperspirant cosmetic agents according to the invention, because a drier skin feel is thereby achieved. Furthermore, it can be preferred in the context of the present invention if the antiperspirant cosmetic agents include a non-volatile silicone oil and/or a non-volatile non-silicone oil in order to mask insoluble constituents, such as talc or ingredients that are dried on the skin.

Especially preferred according to the invention is the use of mixtures of non-volatile and volatile cosmetic oils, because in this way parameters such as skin feel, visibility of the residue, and stability of the antiperspirant cosmetic agent according to the invention can be set and the agent can thus be better adapted to the needs of the consumers.

The volatile and non-volatile silicone oils and volatile and non-volatile non-silicone oils that can be used in the context of the present invention are disclosed, for example, in laid-open applications DE 102010063250 A1 and DE 102012222692 A1.

According to a preferred embodiment of the present invention, the cosmetic oil that is liquid at 20° C. and 1,013 hPa is included in a total amount of 0.02 to 98 wt %, preferably 2 to 85 wt %, preferably 4 to 75 wt %, more preferably 6 to 70 wt %, even more preferably 8 to 60 wt %, particularly 8 to 20 wt %, with respect to the total weight of the antiperspirant cosmetic agent.

At least one odorous substance can also be included as constituent a) of the cosmetic agents according to the invention. However, mixtures of different odorous substances that together produce a pleasant scent are preferably used. Odorous substances that are usable in the context of the present invention are disclosed, for example, in laid-open application DE 102010063250 A1.

Especially pleasant-smelling antiperspirant cosmetic agents according to the invention are obtained if the at least one odorous substance is included in a total amount of 0.00001 to 15 wt %, preferably 0.001 to 9 wt %, more preferably 0.01 to 8 wt %, even more preferably 0.1 to 7 wt %, even more preferably 0.2 to 6 wt %, particularly 0.2 to 2 wt %, with respect to the total weight of the antiperspirant cosmetic agent.

Furthermore, the antiperspirant cosmetic agents according to the invention can include a wax as constituent a). Said wax is preferably selected from the group of (i) fatty acid glycerol mono-, di-, and triesters; (ii) Butyrospermum Parkii (Shea Butter); (iii) esters of saturated, monohydric $C_{8-18}$ alcohols with saturated $C_{12-18}$ monocarboxylic acids; (iv) linear, primary $C_{12-24}$ alkanols; (v) esters of a saturated, monohydric $C_{16-60}$ alkanol and a saturated $C_{8-36}$ monocarboxylic aid; (vi) glycerol triesters of saturated linear $C_{12-30}$ carboxylic acids, which can be hydroxylated; (vii) natural plant waxes; (viii) animal waxes; (ix) synthetic waxes; and (x) mixtures thereof. Waxes that can be used with preference in the context of the present invention are disclosed in laid-open application DE 102012222692 A1.

In the context of the present invention, it is preferred if the wax is included in a total amount of 0.01 to 50 wt %, preferably 3 to 40 wt %, more preferably 5 to 30 wt %, particularly 6 to 25 wt %, with respect to the total weight of the antiperspirant cosmetic agent.

According to one embodiment of the present invention, it can be provided that the antiperspirant cosmetic agents according to the invention include a propellant in a total amount of 0 to 99 wt %, with respect to the total weight of the antiperspirant cosmetic agent, as constituent b). If the cosmetic agents according to the invention include a propellant, said propellant is preferably included in a total amount of 1 to 98 wt %, preferably 20 to 90 wt %, more preferably 30 to 85 wt %, particularly 40 to 75 wt %, with respect to the total weight of the antiperspirant cosmetic agent. In this case, the cosmetic agents according to the invention are formulated as propellant-gas-driven aerosols. Preferred propellants (propellant gases) are propane, propene, n-butane, isobutane, isobutylene, n-pentane, pentene, isopentane, isopentene, methane, ethane, dimethyl ether, nitrogen, air, oxygen, nitrous oxide, 1,1,1,3-tetrafluoroethane, heptafluoro-n-propane, perfluoroethane, monochlorodifluoromethane, 1,1-difluoroethane, tetrafluoropropene, individually and in mixtures thereof. Hydrophilic propellant gases, such as carbon dioxide, can also be advantageously used according to the present invention if the proportion of hydrophilic gases is low and lipophilic propellant gas (e.g., propane/butane) is present in excess. Propane, n-butane, isobutane, and mixtures of these propellant gases are especially preferred. It has been found that the use of n-butane as a sole propellant gas can be especially preferred according to the invention.

The antiperspirant cosmetic agent according to the invention includes at least one specific protein from legumes of the genus *Pisum* and/or *Phaseolus* and/or *Vigna* and/or *Macrotyloma* or from cruciferous plants of the genus *Brassica* as a third constituent c). The genus having the Latin name *Pisum* refers to legumes in the form of peas and comprises, for example, the round pea (also called smooth pea or round-seeded pea), the wrinkled pea, the sugar pea (also called mangetout pea or snow pea), and the giant pea. Legumes in the form of beans, such as the lima bean, the tepary bean, the scarlet runner bean, the haricot bean, and the green bean (also called bush bean or pole bean), fall under the Latin name *Phaseolus*. Legumes having the Latin name *Vigna*, such as the mat bean, the adzuki bean, black gram, the mung bean, the Bambara groundnut, and the rice bean, and the legumes having the Latin name *Macrotyloma*, such as the ground bean or horse gram, likewise exist in the form of beans. The genus having the Latin name *Brassica* refers to cabbage plants. Within these cabbage plants, proteins that can be isolated from cultivated plants from the genus of the cabbage plants are preferred in particular. According to the invention, proteins that can be isolated from rape are especially preferably used. Proteins that can be isolated from rape seeds have proven especially advantageous.

In the context of the present invention, an especially effective reduction in axillary sweat by means of the at least one specific protein is achieved if the at least one protein is included in a total amount of 0.5 to 60 wt %, preferably 1.0 to 50 wt %, more preferably 1.5 to 40 wt %, even more preferably 2.0 to 30 wt %, particularly 2.0 to 20 wt %, with respect to the total weight of the antiperspirant cosmetic agent. With no intention of being restricted to this theory, the use of the aforementioned amounts of the at least one specific protein results in a significant effect on the sweat gland(s) due to gel formation by the protein in the excretory ducts of the sweat glands or due to an effect on the charge equilibrium within the sweat gland(s). In this way, excellent antiperspirant action is ensured. Furthermore, the use of the aforementioned amounts of the at least one specific protein does not lead to unstable formulations, and therefore the stability of the antiperspirant cosmetic agents according to the invention is ensured even over long time periods of storage.

Especially good results with respect to the reduction of axillary moisture and with respect to skin compatibility and storage stability are obtained if the at least one protein has an average molecular weight $M_w$ of 150 to 100,000 Da, preferably 180 to 50,000 Da, more preferably 200 to 10,000 Da, even more preferably 250 to 8,000 Da, particularly 300 to 5,000 Da. The average molecular weight $M_w$ can be determined by gel permeation chromatography (GPC), for example (Andrews, P.; "*Estimation of the Molecular Weights of Proteins by Sephadex Gel-Filtration*"; Biochem. J., 1964, 91, pages 222 to 233).

According to a preferred embodiment of the present invention, the at least one protein has an isoelectric point that lies in the range of pH 4.0 to pH 10.0, preferably pH 4.0 to pH 9.5, particularly pH 4.0 to pH 8.0. In particular, proteins that have an isoelectric point in the aforementioned pH range have proven advantageous in the context of the present invention with respect to the antiperspirant action and the stability of the cosmetic agents according to the invention.

Especially high antiperspirant action, skin compatibility, and storage stability are ensured in the context of the present invention if the at least one protein causes a change in the light absorption in the event of a pH value change of at least 0.5 in a pH range of pH 4.5 to pH 7.5, particularly pH 5.0 to pH 7.0, at a concentration of 0.001 to 10 wt % of protein, with respect to the total weight of the sample mixture used for pH measurement, and at a temperature of 20° C. With no intention of being restricted to this theory, the use of the at least one specific protein that causes a change in the light absorption in a certain pH range results in a significantly increased effect on the sweat gland(s) due to pH-selective gel formation in the excretory ducts of the sweat glands or due to disturbance of the charge equilibrium of the sweat gland(s), so that excellent antiperspirant action of the cosmetic agents according to the invention is ensured, which antiperspirant action is comparable to the antiperspirant action of aluminum-salt-containing or aluminum-zirconium-salt-containing cosmetic agents of the prior art.

In the context of the present invention, it is preferred if the pH value change is achieved by the addition of hydrogencarbonates or carbonates, particularly sodium hydrogencarbonates.

According to a preferred embodiment of the present invention, the at least one protein is selected from the group of (i) unmodified proteins; (ii) hydrolyzed proteins; (iii) chemically modified proteins, particularly hydrophobically and/or cationically and/or anionically modified proteins; (iv) physically modified proteins, particularly fractionated and/or purified and/or irradiated proteins; (v) hydrolyzed unmodified proteins; (vi) hydrolyzed and chemically modified proteins, particularly hydrolyzed and hydrophobically and/or cationically and/or anionically modified proteins; (vii) hydrolyzed and physically modified proteins, particularly fractionated and/or purified and/or irradiated proteins; and (viii) mixtures thereof.

According to the invention, the term "unmodified proteins" should be understood to mean proteins that have been treated neither by means of chemical methods, such as hydrolysis or chemical modification, nor by means of physical methods, such as purification, separation, or irradiation.

Furthermore, according to the invention, the term "hydrolyzed proteins" or "protein hydrolysates" should be understood to mean proteins that are produced by chemical, particularly alkaline or acidic, hydrolysis, by enzymatic hydrolysis, and/or by a combination of both types of hydrolysis. All hydrolytically active enzymes, such as alkaline proteases, are suitable for enzymatic decomposition. Overviews of the production of protein hydrolysates have been presented, for example, by G. Schuster and A. Domsch in Seifen Öle Fette Wachse 108, (1982) 177 and Cosm. Toil. 99, (1984) 63, by H. W. Steisslinger in Parf. Kosm. 72, (1991) 556, and by F. Aurich et al. in Tens. Surf. Det. 29, (1992) 389. Mixtures of individual amino acids that are obtained merely by mixing the pure substances of the amino acids and total hydrolysates that consist merely of individual amino acids do not fall under the term "hydrolyzed proteins" or "protein hydrolysates" in the context of the present invention.

Furthermore, in the context of the present invention, the term "chemically modified proteins" should be understood to mean proteins that are obtained by chemically reacting the reactive groups of the proteins, particularly the hydroxy, amine, imidazole, guanidino, and/or thiol groups of the side chains of the amino acids of the protein, with hydrophobic and/or cationic and/or anionic compounds.

In addition, in the sense of the present invention, the term "physically modified proteins" should be understood to mean proteins that have been modified by physical action, particularly by heat and/or light and/or fractionation.

In the context of this embodiment, it is especially preferred if the at least one protein is selected from the group of chemically modified, particularly hydrophobically modified, proteins. In this context, the hydrophobically modified protein has one or more $C_{4-30}$ hydrocarbon chains, wherein the $C_{4-30}$ hydrocarbon chains can be linear, cyclic, branched, unbranched, saturated, unsaturated, and aromatic and wherein the $C_{4-30}$ hydrocarbon chains are bonded to the protein residue by means of ether and/or ester and/or amine and/or amide bonds.

Furthermore, it is preferred in the context of this embodiment if the at least one protein is selected from the group of chemically modified, particularly cationically modified, proteins. The cationically modified protein therefore preferably includes one or more residues of the formula $R^1$—$N^+(CH_3)_2$—$CH_2$—$CH(OH)$—$CH_2$—$X$—$R$, in which $R^1$ represents an alkyl group having 1 to 30 carbon atoms, an alkenyl group having 1 to 30 carbon atoms, a hydroxyalkyl group having 1 to 30 carbon atoms, particularly a methyl group, a $C_{10-18}$ alkyl, or a $C_{10-18}$ alkenyl group, X represents O, N, or S, and R represents the protein residue. The cationization of the proteins with the residues described above can be achieved by reacting the proteins with the corresponding halides of the formula above, wherein the residues described above can be bonded to the protein by means of ether and/or ester and/or amide and/or amine bonds. In the context of the present invention, the term "protein residue" should be understood to mean the backbone of the corresponding protein to which the cationic group is bonded by means of the previously mentioned bonds, which backbone is formed by the linking of amino acids.

With respect to the antiperspirant action, the skin compatibility, and the storage stability of the cosmetic agents according to the invention, it is especially preferred if the at least one protein is a protein isolated from legumes of the genus *Pisum*, wherein the protein is hydrolyzed and is optionally cationically modified. With no intention of being restricted to this theory, the use of these specific proteins results in a significantly increased effect on the sweat gland(s) due to pH-selective gel formation or due to disturbance of the charge equilibrium within the excretory ducts of the sweat glands. In this way, excellent antiperspirant action of the cosmetic agents according to the invention is ensured, which antiperspirant action is comparable to the antiperspirant action of aluminum-salt-containing or aluminum-zirconium-salt-containing cosmetic agents of the prior art. Furthermore, the use of these specific proteins does not lead to negative interaction with further ingredients in the antiperspirant cosmetic agent, and therefore high storage stability of the antiperspirant cosmetic agents according to the invention is ensured. In addition, the cosmetic agents according to the invention have high skin compatibility.

According to another, especially preferred embodiment of the present invention, the at least one protein causes a change in the light absorption of 1.5 to 90%, preferably 2 to 80%, more preferably 2.5 to 70%, even more preferably 3 to 65%, particularly 3.5 to 60%. In particular, proteins from legumes of the genus *Pisum* and/or *Phaseolus* and/or *Vigna* and/or *Macrotyloma* or from cruciferous plants of the genus *Brassica* that cause the previously mentioned change in the light absorption lead to excellent antiperspirant action in the context of the present invention. The change in the light absorption can occur by a change in the light transmittance of the sample mixture, particularly as a result of opacification, and by the absorption of light by the sample mixture, particularly by the protein itself.

The changes in the light absorption in the event of a pH value change of at least 0.5, which form the basis of this invention, can be determined by measuring the light transmission of a light beam through the sample mixture. The measurements of the light transmission are performed in mV (resolution of 0.1 mV) at a wavelength of 574 nm (greenish yellow) in an open sample vessel at 23° C. and 1,013 mbar by using a Metrohm Optrode 6.1115.000. The pH value change in the pH range of 4.0 to 8.0 is achieved by slowly and continuously adding a carbonate or hydrogencarbonate solution, preferably a 1 wt % sodium hydrogencarbonate solution, to the sample mixture while measuring the pH value with a pH electrode and while stirring at a speed of 750 to 850 rpm. The change in the light absorption that is caused by the at least one protein is calculated in accordance with the formula $\Delta L=[(|L_i|/|L_0|)]*100$. In this formula, $L_i$ represents the light transmission after a change in the pH value by at least 0.5 in the pH range of 4.0 to 8.0, preferably pH 4.5 and 7.5, particularly pH 5.0 and 7.0. In this formula, $L_0$ represents the difference of the light transmission at pH 4.0 and at pH 8.0, preferably at pH 4.5 and at pH 7.5, particularly at pH 5.0 and at pH 7.0, for example light transmission at pH 8.0 minus light transmission at pH 4.0. The at least one specific protein in the antiperspirant cosmetic agents according to the invention causes a change in the light absorption of 1 to 100%, said change being determined in accordance with the method above. However, the present invention is not restricted to antiperspirant cosmetic preparations that include at least one specific protein that causes a change in the light absorption of 1 to 100%, said change being determined in accordance with the method above. The present invention also comprises antiperspirant cosmetic compositions that include at least one specific protein that causes a change in the light absorption of 1 to 100% in accordance with other methods.

In the context of the present invention, it is preferred if the concentration of the at least one protein in the mixture used to determine the change in the light absorption is 0.005 to 10 wt %, preferably 0.05 to 5 wt %, more preferably 0.07 to 3 wt %, particularly 0.09 to 2 wt %, with respect to the total weight of the sample mixture used to determine the change in the light absorption.

According to the invention, the at least one protein preferably causes a change in the light absorption in the event of a pH value change of at least 0.5 and at most 3.5, more preferably at least 0.5 and at most 2.5, particularly at least 0.5 and at most 1.5. In particular, the change in the pH value can be achieved by adding acids or bases, preferably bases in the form of carbonates or hydrogencarbonates, in the appropriate amount.

According to another, preferred embodiment of the present invention, the antiperspirant cosmetic agent has a pH value of pH 2 to pH 10. Within this range, a stable formulation of the cosmetic agents according to the invention is possible without the occurrence of undesired interactions between the ingredients of the antiperspirant cosmetic agents according to the invention. According to the invention, the desired pH value can be set by using acids and bases that are known to a person skilled in the art and are common in antiperspirant cosmetic agents.

According to the invention, it is also preferred if the antiperspirant cosmetic agent additionally includes at least one preservative agent. Preservative agents preferred according to the invention are formaldehyde releaser, iodopropynyl butylcarbamate, parabens, phenoxyethanol, ethanol, benzoic acid and salts thereof, dibromodicyanobutane, 2-bromo-2-nitropropane-1,3-diol, imidazolidinyl urea, 5-chloro-2-methyl-4-isothiazolin-3-one, 2-chloroacetamide, benzalkonium chloride, benzyl alcohol, salicylic acid, and salicylates. Other preservative agents that are usable in the context of the present invention are the substances listed in Annex 6 of the Cosmetics Regulation and cosmetic raw substances having preservative properties or raw substances that support or intensify the preservative action of the aforementioned preservative agents. The preservative agents are preferably included in a total amount of 0.01 to 10 wt %, preferably 0.1 to 7 wt %, more preferably 0.2 to 5 wt %, particularly 0.3 to 2.0 wt %, with respect to the total weight of the antiperspirant cosmetic agent.

In the context of the present invention, it is preferred if the antiperspirant cosmetic agent exists in the form of a water-in-oil emulsion. In particular, the water-in-oil emulsion can be a sprayable water-in-oil emulsion, which can be sprayed by means of a propellant. In this context, it is preferred if the antiperspirant cosmetic agent according to the invention existing in the form of a water-in-oil emulsion includes the at least one protein in a total amount of 0.1 to 70 wt %, preferably 0.5 to 60 wt %, more preferably 1.0 to 50 wt %, even more preferably 1.5 to 40 wt %, even more preferably 2.0 to 30 wt %, particularly 2.0 to 20 wt %, with respect to the total weight of the antiperspirant cosmetic agent.

However, it can be equally preferred according to the invention if the antiperspirant cosmetic agent exists as an oil-in-water emulsion. In this case, the cosmetic agent according to the invention is preferably sprayed as a propellant-free pump spray or squeeze spray or applied as a roll-on. In this context, it is preferred if the antiperspirant cosmetic agent existing in the form of an oil-in-water emulsion includes the at least one protein in a total amount of 0.1 to 70 wt %, preferably 0.5 to 60 wt %, more preferably 1.0 to 50 wt %, even more preferably 1.5 to 40 wt %, even more preferably 2.0 to 30 wt %, particularly 2.0 to 20 wt %, with respect to the total weight of the antiperspirant cosmetic agent.

According to another, preferred embodiment of the present invention, the cosmetic agents according to the invention can include only a small content of free water or no free water. In the sense of the present invention, the term "free water" is understood to mean water that is different from water of crystallization, hydration water, or similarly molecularly bound water of the constituents that are used. The antiperspirant cosmetic agent preferably includes free water in a total amount of less than 10 wt %, preferably less than 8 wt %, more preferably less than 5 wt %, even more preferably less than 3 wt %, even more preferably less than 1 wt %, particularly 0 wt %, with respect to the total weight of the antiperspirant cosmetic agent.

However, in the context of a further embodiment, it is also preferred according to the invention if the antiperspirant cosmetic agent exists as an aqueous, aqueous-alcoholic, or aqueous-glycolic solution. According to the invention, because the cosmetic agents according to the invention include no antiperspirant aluminum and/or zirconium halides and/or hydroxyhalides, which have reduced antiperspirant action as a result of the addition of protic solvents, protic solvents such as aqueous solutions can be used to formulate the antiperspirant cosmetic agents according to the invention without the occurrence of a significant reduction in the antiperspirant action. Therefore, the addition of the at least one specific protein ensures effective influencing of the sweat gland(s) and thus excellent antiperspirant action even if protic solvents are used.

In the context of this embodiment of the present invention, it was surprisingly found that the effect on the sweat gland(s) by the at least one specific protein can be significantly increased if the antiperspirant cosmetic agents according to the invention include free water in an amount of 5 to 99 wt %, with respect to the total weight of the antiperspirant cosmetic agent. Therefore, in an especially preferred embodiment of the present invention, the antiperspirant cosmetic agent includes free water in a total amount of 5 to 96 wt %, preferably 15 to 80 wt %, more preferably 30 to 70 wt %, particularly 40 to 60 wt %, with respect to the total weight of the antiperspirant cosmetic agent.

Furthermore, in the context of this embodiment, it is preferred if the antiperspirant cosmetic agent includes ethanol in a total amount of 1 to 99 wt %, preferably 5 to 70 wt %, preferably 7 to 50 wt %, particularly 10 to 30 wt %, with respect to the total weight of the antiperspirant cosmetic agent. As previously stated, because of the use of the at least one specific protein, even high amounts of protic solvents such as ethanol can be used without the antiperspirant action of the antiperspirant cosmetic agent according to the invention being negatively affected.

The antiperspirant cosmetic agent according to the invention can be applied by means of various methods. According to a preferred embodiment, the antiperspirant cosmetic agent is formulated as a spray application. The spray application is accomplished by means of a spraying device, which includes a filling of the antiperspirant cosmetic agent according to the invention, which is liquid, viscously flowable, in the form of a suspension, or in the form of a powder, in a container. The filling can be under the pressure of a propellant (compressed-gas cans, compressed-gas packages, aerosol packages), or a mechanically operated pump atomizer without propellant gas (pump sprays/squeeze bottle) can be used. The antiperspirant cosmetic agent can be atomized physically, mechanically, or electromechanically, for example by means of piezoelectric effects or electric pumps. Containers and removal devices that are usable in the context of this embodiment are described, for example, in laid-open application DE 102012222692 A1.

Furthermore, the antiperspirant cosmetic agent can preferably be formulated as a stick, soft solid, cream, gel, roll-on, or loose or compact powder. The formulation of the antiperspirant cosmetic agents according to the invention in a certain product form, such as an antiperspirant roll-on, an antiperspirant stick, or an antiperspirant gel, is preferably based on the requirements of the intended use. Therefore, depending on the intended use, the antiperspirant cosmetic agents according to the invention can exist in solid, semi-solid, liquid, disperse, emulsified, suspended, gel, multi-phase, or powdery form. In the sense of the present invention, all types of solid dispersions in liquids also fall under the term "liquid." Furthermore, in the sense of the present invention, agents that have at least two different phases having a phase separation and in the case of which the phases can be arranged horizontally, i.e., one over the other, or vertical, i.e., one next to the other, are understood by multi-phase antiperspirant cosmetic agents according to the invention. The application can be performed, for example, by means of a roller-ball applicator or by means of a solid stick.

In the context of the present invention, it can also be preferred if the antiperspirant cosmetic agent is included on and/or in a disposable substrate, selected from the group of wipes, pads, and puffs. Especially preferred are wet wipes, i.e., preferably individually packaged wet wipes prefabricated for the user, which are well known, for example, from the field of glass cleaning or from the field of wet toilet wipes. Such wet wipes, which can advantageously also include preservative substances, are impregnated or loaded with an antiperspirant cosmetic agent according to the invention and are preferably packaged individually. Preferred substrate materials are selected from porous flat wipes. These wipes include wipes composed of woven and nonwoven synthetic and natural fibers, felt, paper, or foam, such as hydrophilic polyurethane foam. Deodorizing or antiperspirant substrates preferred according to the invention can be obtained by soaking or impregnation or by applying an antiperspirant cosmetic agent according to the invention to a substrate in melted form.

According to the invention, it is preferred that the antiperspirant cosmetic agent includes at least one further auxiliary substance, selected from the group of (i) emulsifiers and/or surfactants; (ii) thickeners; (iii) chelating agents; (iv) deodorant active substances; (v) mono- and/or polyhydric alcohols and/or polyethylene glycols; (vi) skin-cooling active substances; (vii) pH adjusters; (viii) skin care active substances, such as moisturizers, skin-soothing substances, skin-lightening substances, skin-smoothing substances; and (ix) mixtures thereof.

Suitable emulsifiers and surfactants preferred according to the invention are selected from anionic, cationic, non-ionic, amphoteric, particularly ampholytic and zwitterionic emulsifiers and surfactants. Surfactants are amphiphilic (bi-functional) compounds that consist of at least one hydrophobic molecule part and at least one hydrophilic molecule part. The hydrophobic residue is preferably a hydrocarbon chain having 8 to 28 carbon atoms, which hydrocarbon chain can be saturated or unsaturated, linear or branched. This $C_8$-$C_{28}$ alkyl chain is especially preferably linear. Emulsifiers and surfactants that are usable with preference in the context of the present invention are disclosed, for example, in laid-open applications DE 102012222692 A1, DE 102010063250 A1, and DE 102010055816 A1.

To thicken the antiperspirant cosmetic agents according to the invention, preferably substances selected from the following are used: cellulose ethers, xanthan gum, sclerotium gum, succinoglucans, polygalactomannans, pectins, agar, carrageenan, tragacanth, gum arabic, gum karaya, tara gum, gellan gum, gelatin, propylene glycol alginate, alginic acids and salts thereof, polyvinylpyrrolidones, polyvinyl alcohols, polacrylamides, starches that are physically modified (e.g., by means of pre-gelatinization) and/or chemically modified, acrylic acid/acrylate copolymers, acrylic acid/acrylamide copolymers, acrylic acid/vinylpyrrolidone copolymers, acrylic acid/vinylformamide copolymers, and polyacrylates. Furthermore, especially preferred thickeners are selected from carbomers. Carbomers are thickening cross-linked polymers of acrylic acid, methacrylic acid, and salts thereof. The cross-linking can be accomplished by means of polyfunctional compounds such as polyalkylene ethers of polysaccharides or of polyalcohols, such as sucrose allyl ethers, pentaerythritol allyl ethers, propylene allyl ethers. Homopolymers of acrylic acid or salts thereof that are cross-linked by means of a pentaerythritol allyl ether, a sucrose allyl ether, or a propylene allyl ether are preferred in the context of the present invention. A copolymer of $C_{10-30}$ alkyl acrylate, acrylic acid, methacrylic acid, and esters thereof that is cross-linked by means of a sucrose allyl ether or a pentaerythritol allyl ether is a thickener that is usable in the context of the present invention. The products available under the trade name Carbopol® (BF Goodrich, Ohio, USA), such as Carbopol 934, Carbopol 940, Carbopol 941, Carbopol 971, Carbopol 974, Carbopol EZ2, Carbopol ETD 2001, Carbopol ETD 2020, Carbopol ETD 2050, Carbopol ultrez 10, Carbopol ultrez 20, or Carbopol ultrez 21 are thickeners based on carbomers.

Furthermore, lipophilic thickeners can be used to thicken the antiperspirant cosmetic agents according to the invention. Lipophilic thickeners preferred according to the invention are selected from hydrophobed clay minerals, bentonites, pyrogenic silicic acids, and derivatives thereof.

To further support the effect of the at least one specific protein on the sweat gland(s), it can be advantageous to add at least one chelating agent to the antiperspirant cosmetic agents according to the invention in a total amount of 0.01 to 3.0 wt %, preferably 0.02 to 1.0 wt %, particularly 0.05 to 0.1 wt %, with respect to the total weight of the antiperspirant agent according to the invention. In the context of the present invention, preferred chelating agents are selected from the group of β-alanine diacetic acid, cyclodextrin, diethylenetriamine penta(methylene phosphonic acid), sodium, potassium, calcium disodium, ammonium, and triethanolamine salts of ethylenediamine tetraacetic acid (EDTA), etidronic acid, hydroxyethyl ethylenediamine tetraacetic acid (HEDTA) and sodium salts thereof, sodium salts of nitrilotriacetic acid (NTA), diethylenetriamine pentaacetic acid, phytic acid, hydroxypropyl cyclodextrin, methyl cyclodextrin, pentasodium amino trimethylene phosphonate, pentasodium ethylenediamine tetramethylene phosphonate, pentasodium diethylenetriaminepentaacetate, pentasodium triphosphate, potassium EDTMP, sodium EDTMP, sodium dihydroxyethylglycinate, sodium phytate, sodium polydimethylglycinophenol sulfonate, tetrahydroxyethyl ethylenediamine, tetrahydroxypropyl ethylenediamine, tetrapotassium etidronate, tetrasodium etidronate, tetrasodium iminodisuccinate, trisodium ethylenediamine disuccinate, tetrasodium N,N-bis(carboxymethyl)-glutamate, tetrasodium DL-alanine-N,N-diacetate, and desferrioxamine.

The deodorizing action of the antiperspirant cosmetic agents according to the invention can be increased further if at least one deodorant active substance having antibacterial and/or bacteriostatic and/or enzyme-inhibiting and/or odor-neutralizing and/or odor-absorbing action is included in a total amount of 0.0001 to 40 wt %, preferably 0.2 to 20 wt %, more preferably 1 to 15 wt %, particularly 1.5 to 5 wt %, with respect to the total weight of the antiperspirant cosmetic agent according to the invention. If ethanol is used in the agents according to the invention, the ethanol is not considered to be a deodorant active substance in the context of the present invention, but rather a constituent of the carrier. Deodorant active substances preferred according to the invention are disclosed, for example, in laid-open application DE 102010063250 A1.

Preferred antiperspirant cosmetic agents according to the invention also include at least one water-soluble polyhydric $C_{2-9}$ alkanol having 2 to 6 hydroxyl groups and/or at least one water-soluble polyethylene glycol having 3 to 50 ethylene oxide units and mixtures thereof. The aforementioned deodorant active substances in the form of 1,2-alkanediols do not fall thereunder. Preferred alkanols and water-soluble polyethylene glycols are described, for example, in laid-open application DE 102010063250 A1.

According to another embodiment of the present invention, the antiperspirant cosmetic agents also include at least one skin-cooling active substance. Skin-cooling active substances suitable according to the invention are, for example, menthol, isopulegol, and menthol derivatives, e.g., menthyl lactate, menthyl glycolate, menthyl ethyl oxamate, menthyl pyrrolidone carboxylic acid, menthyl methyl ether, menthoxypropanediol, menthone glycerin acetal (9-methyl-6-(1-methylethyl)-1,4-dioxaspiro[4.5]decane-2-methanol), monomenthyl succinate, 2-hydroxymethyl-3,5,5-trimethyl-cyclohexanol, and 5-methyl-2-(1-methylethyl)cyclohexyl-N-ethyloxamate. Menthol, isopulegol, menthyl lactate, menthoxypropanediol, menthyl pyrrolidone carboxylic acid, and 5-methyl-2-(1-methylethyl)cyclohexyl-N-ethyloxamate and mixtures of these substances, particularly mixtures of menthol and menthyl lactate, menthol, menthol glycolate, and menthyl lactate, menthol and menthoxypropanediol, or menthol and isopulegol, are preferred as skin-cooling active substances.

According to the invention, preferably acids and/or alkalizing agents and/or buffers are used as pH adjusters. According to the invention, preferably inorganic acids (such as hydrochloric acid, sulfuric acid, or phosphoric acid) or organic acids (such as citric acid, tartaric acid, or malic acid) are used as acids. The alkalizing agents that are usable according to the invention are preferably selected from the group consisting of ammonia, basic amino acids, alkali hydroxides, carbonates and hydrogencarbonates, alkanolamines, such as amino-2-methyl-1-propanol, monoethanolamine, triethanolamine, diethanolamine, and triisopropanolamine, alkali metal metasilicates, urea, morpholine, N-methylglucamine, imidazole, alkali phosphates, and alkali hydrogenphosphates. Preferably lithium, sodium, or potassium, particularly sodium or potassium, is used as an alkali metal ion. In particular, carbonic acid/bicarbonate buffer, carbonic acid/silicate buffer, acetic acid/acetate buffer, phosphate buffer, ammonia buffer, citric acid or citrate buffer, buffer based on tris(hydroxymethyl)aminomethane, buffer based on 4-(2-hydroxyethyl)-1-piperazineethanesulfonic acid, buffer based on 4-(2-hydroxyethyl)piperazine-1-propanesulfonic acid, buffer based on 2-(N-morpholino)ethanesulfonic acid, and barbital/acetate buffer are suitable as buffer systems in the context of the present invention. The appropriate buffer system is selected on the basis of the desired pH value of the antiperspirant cosmetic agents according to the invention.

In a preferred embodiment, the antiperspirant cosmetic agents according to the invention are characterized in that said agents include—with respect to the total weight of the antiperspirant cosmetic agent according to the invention—
  at least one protein in a total amount of 0.5 to 60 wt %, preferably 1.0 to 50 wt %, more preferably 1.5 to 40 wt %, even more preferably 2.0 to 30 wt %, particularly 2.0 to 20 wt %,
  12 to 98 wt %, preferably 25 to 55 wt %, more preferably 30 to 50 wt %, particularly 35 to 45 wt %, of water,
  at least one emulsifier and/or one surfactant,
  at least one pH adjuster,
  at least one preservative agent, and
  at least one substance selected from the group of cosmetic oils that are liquid at 20° C. and 1,013 hPa, odorous substances, and waxes,
wherein the at least one protein occurs in legumes of the genus *Pisum* and/or *Phaseolus* and/or *Vigna* and/or *Macrotyloma* or in cruciferous plants of the genus *Brassica* and wherein the at least one protein causes a change in the light absorption of 1 to 100% in the event of a pH value change of at least 0.5 in a pH range of pH 4.0 to pH 8.0, at a temperature of 20° C. to 40° C. and a concentration of the protein of 0.001 to 10 wt %, with respect to the total weight of the sample mixture used to determine the change in the light absorption.

In another preferred embodiment, the antiperspirant cosmetic agents according to the invention are characterized in that said agents include—with respect to the total weight of the antiperspirant cosmetic agent according to the invention—
- at least one protein in a total amount of 0.5 to 60 wt %, preferably 1.0 to 50 wt %, more preferably 1.5 to 40 wt %, even more preferably 2.0 to 30 wt %, particularly 2.0 to 20 wt %,
- 12 to 98 wt %, preferably 25 to 55 wt %, more preferably 30 to 50 wt %, particularly 35 to 45 wt %, of water,
- at least one emulsifier and/or one surfactant,
- at least one pH adjuster,
- at least one preservative agent,
- 0.01 to 2 wt %, preferably 0.1 to 1 wt %, more preferably 0.2 to 0.7 wt %, particularly 0.3 to 0.5 wt %, of a thickener, and
- at least one substance selected from the group of cosmetic oils that are liquid at 20° C. and 1,013 hPa, odorous substances, and waxes, wherein the at least one protein occurs in legumes of the genus *Pisum* and/or *Phaseolus* and/or *Vigna* and/or *Macrotyloma* or in cruciferous plants of the genus *Brassica* and wherein the at least one protein causes a change in the light absorption of 1 to 100% in the event of a pH value change of at least 0.5 in a pH range of pH 4.0 to pH 8.0, at a temperature of 20° C. to 40° C. and a concentration of the protein of 0.001 to 10 wt %, with respect to the total weight of the sample mixture used to determine the change in the light absorption.

In a preferred embodiment, the antiperspirant cosmetic agents according to the invention are characterized in that said agents include—with respect to the total weight of the antiperspirant cosmetic agent according to the invention—
- at least one protein in a total amount of 0.5 to 60 wt %, preferably 1.0 to 50 wt %, more preferably 1.5 to 40 wt %, even more preferably 2.0 to 30 wt %, particularly 2.0 to 20 wt %,
- 12 to 98 wt %, preferably 25 to 55 wt %, more preferably 30 to 50 wt %, particularly 35 to 45 wt %, of water,
- at least one propellant in a total amount of 1 to 98 wt %, preferably 20 to 90 wt %, more preferably 30 to 85 wt %, particularly 40 to 75 wt %,
- at least one emulsifier and/or one surfactant,
- at least one pH adjuster,
- at least one preservative agent, and
- at least one substance selected from the group of cosmetic oils that are liquid at 20° C. and 1,013 hPa, odorous substances, and waxes, wherein the at least one protein occurs in legumes of the genus *Pisum* and/or *Phaseolus* and/or *Vigna* and/or *Macrotyloma* or in cruciferous plants of the genus *Brassica* and wherein the at least one protein causes a change in the light absorption of 1 to 100% in the event of a pH value change of at least 0.5 in a pH range of pH 4.0 to pH 8.0, at a temperature of 20° C. to 40° C. and a concentration of the protein of 0.001 to 10 wt %, with respect to the total weight of the sample mixture used to determine the change in the light absorption.

In another preferred embodiment, the antiperspirant cosmetic agents according to the invention are characterized in that said agents include—with respect to the total weight of the antiperspirant cosmetic agent according to the invention—
- at least one protein in a total amount of 0.5 to 60 wt %, preferably 1.0 to 50 wt %, more preferably 1.5 to 40 wt %, even more preferably 2.0 to 30 wt %, particularly 2.0 to 20 wt %,
- 12 to 98 wt %, preferably 25 to 55 wt %, more preferably 30 to 50 wt %, particularly 35 to 45 wt %, of water,
- at least one propellant in a total amount of 1 to 98 wt %, preferably 20 to 90 wt %, more preferably 30 to 85 wt %, particularly 40 to 75 wt %,
- at least one emulsifier and/or one surfactant,
- at least one pH adjuster,
- at least one preservative agent,
- 0.01 to 2 wt %, preferably 0.1 to 1 wt %, more preferably 0.2 to 0.7 wt %, particularly 0.3 to 0.5 wt %, of a thickener, and
- at least one substance selected from the group of cosmetic oils that are liquid at 20° C. and 1,013 hPa, odorous substances, and waxes, wherein the at least one protein occurs in legumes of the genus *Pisum* and/or *Phaseolus* and/or *Vigna* and/or *Macrotyloma* or in cruciferous plants of the genus *Brassica* and wherein the at least one protein causes a change in the light absorption of 1 to 100% in the event of a pH value change of at least 0.5 in a pH range of pH 4.0 to pH 8.0, at a temperature of 20° C. to 40° C. and a concentration of the protein of 0.001 to 10 wt %, with respect to the total weight of the sample mixture used to determine the change in the light absorption.

In the context of the present invention, it can also be provided that the cosmetic agent according to the invention is formulated as a two-component agent. For this purpose, the individual components are preferably stored in separate containers and are applied to the skin one after the other in any order or simultaneously. Separation into multi-component systems is preferred particularly if incompatibility of the ingredients is expected or feared.

Therefore, another subject of the present invention is a packaging unit (kit of parts), comprising—formulated separate from each other—
a) at least one first container (C1), containing a cosmetic agent (M1) comprising at least one antiperspirant active substance, and
b) at least one second container (C2), containing a cosmetic agent (M2) comprising at least one protein, wherein the at least one protein occurs in legumes of the genus *Pisum* and/or *Phaseolus* and/or *Vigna* and/or *Macrotyloma* or in cruciferous plants of the genus *Brassica*, wherein the at least one protein causes a change in the light absorption of 1 to 100% in the event of a pH value change of at least 0.5 in a pH range of pH 4.0 to pH 8.0, at a temperature of 20° C. to 40° C. and a concentration of the protein of 0.001 to 10 wt %, with respect to the total weight of the sample mixture used to determine the change in the light absorption, and wherein the cosmetic agent (M2) includes no aluminum and/or zirconium halides and/or hydroxyhalides.

According to the invention, the term "antiperspirant active substance" is understood to mean active substances that reduce the perspiration of the sweat glands of the body. However, the proteins from legumes of the genus *Pisum* and/or *Phaseolus* and/or *Vigna* and/or *Macrotyloma* or from cruciferous plants of the genus *Brassica* that are included in the cosmetic agent (M2) and that cause a change in the light absorption under the conditions described above do not fall thereunder.

The statements made with respect to the cosmetic agents according to the invention apply, mutatis mutandis, to the cosmetic agent (M2) in the container (C2).

Another subject of the present invention is the use of a protein to at least partially influence the sweat gland(s), wherein the at least one protein occurs in legumes of the genus *Pisum* and/or *Phaseolus* and/or *Vigna* and/or *Macrotyloma* or in cruciferous plants of the genus *Brassica* and wherein the at least one protein causes a change in the light absorption of 1 to 100% in the event of a pH value change of at least 0.5 in a pH range of pH 4.0 to pH 8.0, at a temperature of 20° C. to 40° C. and a concentration of the protein of 0.001 to 10 wt %, with respect to the total weight of the sample mixture used to determine the change in the light absorption.

According to the invention, "to influence the sweat gland(s)" should be understood to mean to influence the sweat gland(s) in such a way that the secretion of sweat from the excretory duct is avoided or reduced. With no intention of being restricted to one theory, this can be accomplished, for example, by the formation of a gel and/or precipitate of the at least one specific protein in the excretory duct of the sweat gland or the excretory ducts of the sweat glands. Furthermore, the use of the at least one specific protein can, however, also lead to disturbance of the charge equilibrium within the excretory ducts of the sweat glands. The statements made with respect to the cosmetic antiperspirant agents according to the invention apply, mutatis mutandis, to the use according to the invention.

Furthermore, another subject of the present invention is the use of a combination, including
a) at least one substance selected from the group of cosmetic oils that are liquid at 20° C. and 1,013 hPa, odorous substances, and waxes,
b) propellant in a total amount of 0 to 99 wt %, with respect to the total weight of the antiperspirant cosmetic agent, and
c) at least one protein in a total amount of 0.1 to 70 wt %, with respect to the total weight of the antiperspirant cosmetic agent, wherein the at least one protein occurs in legumes of the genus *Pisum* and/or *Phaseolus* and/or *Vigna* and/or *Macrotyloma* or in cruciferous plants of the genus *Brassica*, wherein the at least one protein causes a change in the light absorption of 1 to 100% in the event of a pH value change of at least 0.5 in a pH range of pH 4.0 to pH 8.0, at a temperature of 20° C. to 40° C. and a concentration of the protein of 0.001 to 10 wt %, with respect to the total weight of the sample mixture used to determine the change in the light absorption, and
wherein the combination includes no aluminum and/or zirconium halides and/or hydroxyhalides,
to reduce and/or prevent sweat, particularly axillary sweat or sweat of other body regions.

In the sense of the present invention, the term "combination" comprises a mixture of the ingredients a), b), and c) that are specified above. The statements made with respect to the antiperspirant cosmetic agents according to the invention and to the use according to the invention apply, mutatis mutandis, to the use according to the use of the aforementioned combination.

In addition, another subject of the present invention is an antiperspirant cosmetic agent, including a) at least one substance selected from the group of cosmetic oils that are liquid at 20° C. and 1,013 hPa, odorous substances, and waxes,
b) propellant in a total amount of 0 to 99 wt %, with respect to the total weight of the antiperspirant cosmetic agent, and
c) at least one protein isolated from legumes of the genus *Pisum* in a total amount of 0.1 to 70 wt %, with respect to the total weight of the antiperspirant cosmetic agent, wherein the protein is hydrolyzed and optionally cationically modified, or at least one protein that occurs in rape and/or cauliflower and/or red cabbage and/or savoy cabbage and/or white cabbage and/or pointed cabbage and/or Brussels sprouts and/or kohlrabi and/or curly kale and/or broccoli and/or mustard and/or turnips, which protein preferably occurs in rape seed and is optionally hydrolyzed, in a total amount of 0.1 to 70 wt %, with respect to the total weight of the antiperspirant cosmetic agent,
wherein the antiperspirant cosmetic agent includes no aluminum and/or zirconium halides and/or hydroxyhalides.

The statements made with respect to the antiperspirant cosmetic agents according to the invention, the use according to the invention, and the method according to the invention apply, mutatis mutandis, to other, preferred embodiments of this subject.

Finally, another subject of the present invention is a non-therapeutic cosmetic method for preventing and/or reducing the perspiration of the body, wherein an antiperspirant cosmetic agent according to the invention is applied to the skin, particularly to the skin of the axillae, and remains on the skin of the axillae for at least 1 hour, preferably for at least 2 hours, preferably for at least 4 hours, particularly for at least 6 hours.

In the context of the method according to the invention, it can also be provided, however, that first a cosmetic agent including at least one antiperspirant aluminum and/or zirconium halide and/or hydroxyhalide is applied and then the cosmetic agent according to the invention is applied. But it is also possible that first the cosmetic agent according to the invention is applied and then a cosmetic agent including at least one antiperspirant aluminum and/or zirconium halide and/or hydroxyhalide is used. Furthermore, the antiperspirant cosmetic agent according to the invention and the cosmetic agent including at least one antiperspirant aluminum and/or zirconium halide and/or hydroxyhalide can also be applied to the skin at the same time. The time span between the application of the two agents is 0 seconds to 24 hours. Furthermore, it is preferred if the agents remain on the skin of the axillae for at least 1 hour, preferably for at least 2 hours, more preferably for at least 4 hours, particularly for at least 6 hours, after being applied.

The statements made with respect to the antiperspirant cosmetic agents according to the invention and to the use according to the invention apply, mutatis mutandis, to the method according to the invention.

The following examples illustrate the present invention without restricting the present invention to said examples:

Examples

Formulations:

The protein used in the following examples is preferably a hydrolyzed protein from legumes of the genus *Pisum* having an average molecular weight $M_w$ of approximately 500 Da or a protein that occurs in rape and/or cauliflower and/or red cabbage and/or savoy cabbage and/or white cabbage and/or pointed cabbage and/or Brussels sprouts and/or kohlrabi and/or curly kale and/or broccoli and/or mustard and/or turnips, preferably a protein that occurs in rape seed and is optionally hydrolyzed:

Antiperspirant cosmetic agents according to the invention having a pH of 2.5 to 10.0 (amount specifications in wt %)

|  | 1 | 2 | 3 | 4 | 5 | 6 | 7 |
|---|---|---|---|---|---|---|---|
| Isopropyl myristate | 0.50 | 0.10 | 0.50 | 1.0 | 2.0 | 3.0 | 5.0 |
| Protein | 0.50 | 2.0 | 3.0 | 5.0 | 7.0 | 10 | 20 |
| Eumulgin B3 [a] | 3.0 | 3.0 | 3.0 | 4.0 | 4.0 | 4.0 | 5.0 |
| Perfume | 0.10 | 0.20 | 0.30 | 0.30 | 0.50 | 0.8 | 1.0 |
| Preservative agent | 0.50 | 0.50 | 0.50 | 0.80 | 0.80 | 1.5 | 2.0 |
| pH adjuster | ad pH | ad pH | ad pH | ad pH | ad pH | ad pH | ad pH |
| Water | ad 100 | ad 100 | ad 100 | ad 100 | ad 100 | ad 100 | ad 100 |

[a] Eumulgin B3 (INCI: Ceteareth-30; BASF)

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. An antiperspirant cosmetic agent, comprising:
a) at least one substance selected from the group consisting of cosmetic oils that are liquid at 20° C. and 1,013 hPa, odorous substances, and waxes,
b) propellant in a total amount of 20 to 90 wt %, with respect to the total weight of the antiperspirant cosmetic agent, and
c) at least one protein in a total amount of 0.1 to 70 wt %, with respect to the total weight of the antiperspirant cosmetic agent, wherein the at least one protein is isolated from legumes of the genus Pisum, Phaseolus, Vigna, Macrotyloma and/or from cruciferous plants of genus Brassica and wherein the at least one protein causes a change in the light absorption of 1 to 100% in the event of a pH value change of at least 0.5 in a pH range of pH 4.0 to pH 8.0, at a temperature of 20° C. to 40° C. and a concentration of the protein of 0.001 to 10 wt %, with respect to the total weight of the sample mixture used to determine the change in the light absorption, wherein the change in the light absorption is determined by measuring light transmission of a light beam through the sample mixture, and measurement of the light transmission is performed in resolution of 0.1 mV at a wavelength of 574 nm in an open sample vessel at 23° C. and 1,013 mbar by using a Metrohm Optrode, and wherein the at least one protein is chemically modified,
wherein the antiperspirant cosmetic agent includes no aluminum halides, zirconium halides and hydroxyhalides, and wherein the antiperspirant cosmetic agent provides an antiperspirant effect when applied to a skin surface.

2. The antiperspirant cosmetic agent according to claim 1, wherein the at least one protein is included in a total amount of 0.5 to 60 wt % based on the total weight of the antiperspirant cosmetic agent.

3. The antiperspirant cosmetic agent according to claim 1, wherein the at least one protein is included in a total amount of 1.5 to 50 wt % based on the total weight of the antiperspirant cosmetic agent.

4. The antiperspirant cosmetic agent according to claim 1, wherein the at least one protein is included in a total amount of 2.5 to 30 wt % based on the total weight of the antiperspirant cosmetic agent.

5. The antiperspirant cosmetic agent according to claim 1, wherein the at least one protein is included in a total amount of 3 to 20 wt % based on the total weight of the antiperspirant cosmetic agent.

6. The antiperspirant cosmetic agent according to claim 1, wherein the at least one protein has an average molecular weight $M_w$ of 150 to 100,000 Da.

7. The antiperspirant cosmetic agent according to claim 1, wherein the at least one protein has an average molecular weight $M_w$ of 180 to 50,000 Da.

8. The antiperspirant cosmetic agent according to claim 1, wherein the at least one protein has an average molecular weight $M_w$ of 250 to 8,000 Da.

9. The antiperspirant cosmetic agent according to claim 1, wherein the at least one protein has an average molecular weight $M_w$ of 300 to 5,000 Da.

10. The antiperspirant cosmetic agent according to claim 1, wherein the at least one protein causes a change in the light absorption in the event of a pH value change of at least 0.5 in a pH range of pH 4.5 to pH 7.5, at a concentration of 0.001 to 10 wt % of protein, with respect to the total weight of the sample mixture used for pH measurement, and at a temperature of 20° C.

11. The antiperspirant cosmetic agent according to claim 1, wherein the at least one protein causes a change in the light absorption in the event of a pH value change of at least 0.5 in a pH range of pH 5.0 to pH 7.0, at a concentration of 0.001 to 10 wt % of protein, with respect to the total weight of the sample mixture used for pH measurement, and at a temperature of 20° C.

12. The antiperspirant cosmetic agent according to claim 1, wherein the pH value change is caused by the addition of hydrogencarbonates or carbonates.

13. The antiperspirant cosmetic agent according to claim 1, wherein the at least one protein is a cationically modified protein and the cationically modified protein includes one or more residues of the formula $R^1$—$N^+(CH_3)_2$—$CH_2$—$CH(OH)$—$CH_2$—X—R, in which $R^1$ represents an alkyl group having 1 to 30 carbon atoms, an alkenyl group having 1 to 30 carbon atoms, a hydroxyalkyl group having 1 to 30 carbon atoms, a $C_{10-18}$ alkyl, or a $C_{10-18}$ alkenyl group, X represents O, N, or S, and R represents the protein residue.

14. The antiperspirant cosmetic agent according to claim 1, wherein the at least one protein causes a change in the light absorption of 1.5 to 90%.

15. The antiperspirant cosmetic agent according to claim 1, wherein the at least one protein causes a change in the light absorption in the event of a pH value change of at least 0.5 and at most 3.5.

16. A non-therapeutic cosmetic method for reducing the perspiration of the body, comprising: applying to a skin surface the antiperspirant cosmetic agent of claim 1, wherein the antiperspirant cosmetic agent is left on the skin for at least 1 hour.

17. A packaging unit, comprising, formulated separate from each other:
   a) at least one first container (C1), containing a cosmetic agent (M1) comprising at least one antiperspirant active substance, and
   b) at least one second container (C2), containing a cosmetic agent (M2) comprising at least one protein, wherein the at least one protein is isolated from legumes of the genus Pisum, Phaseolus, Vigna, Macrotyloma, and/or from cruciferous plants of the genus Brassica, wherein the at least one protein causes a change in the light absorption of 1 to 100% in the event of a pH value change of at least 0.5 in a pH range of pH 4.0 to pH 8.0, at a temperature of 20° C. to 40° C. and a concentration of the protein of 0.001 to 10 wt %, with respect to the total weight of the sample mixture used to determine the change in the light absorption, wherein the change in the light absorption is determined by measuring light transmission of a light beam through the sample mixture, and measurement of the light transmission is performed in resolution of 0.1 mV at a wavelength of 574 nm in an open sample vessel at 23° C. and 1,013 mbar by using a Metrohm Optrode, and wherein the at least one protein is chemically modified, wherein the cosmetic agent (M2) includes no aluminum halides, zirconium halides and hydroxyhalides, and wherein the cosmetic agent (M2) provides an antiperspirant effect when applied to a skin surface.

18. An antiperspirant cosmetic agent, comprising:
   a) at least one substance selected from the group consisting of cosmetic oils that are liquid at 20° C. and 1,013 hPa, odorous substances, and waxes,
   b) propellant in a total amount of 20 to 90 wt %, with respect to the total weight of the antiperspirant cosmetic agent, and
   c) at least one protein isolated from legumes of the genus of Pisum in a total amount of 0.1 to 70 wt %, with respect to the total weight of the antiperspirant cosmetic agent, or at least one protein that is isolated from rape, cauliflower, red cabbage, savoy cabbage, white cabbage, pointed cabbage, Brussels sprouts, kohlrabi, curly kale, broccoli, mustard, and/or turnips, in a total amount of 0.1 to 70 wt %, with respect to the total weight of the antiperspirant cosmetic agent, and wherein the at least one protein is chemically modified, wherein the antiperspirant cosmetic agent includes no aluminum halides, zirconium halides and hydroxyhalides, and wherein the antiperspirant cosmetic agent provides an antiperspirant effect when applied to a skin surface.

* * * * *